United States Patent
Qu et al.

(10) Patent No.: US 8,032,213 B1
(45) Date of Patent: Oct. 4, 2011

(54) VENTRICULAR DEFIBRILLATION THRESHOLD ESTIMATION

(75) Inventors: Fujian Qu, Sunnyvale, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 964 days.

(21) Appl. No.: 11/753,890

(22) Filed: May 25, 2007

(51) Int. Cl.
   *A61N 1/08* (2006.01)
(52) U.S. Cl. .................................. 607/7; 607/8; 607/28
(58) Field of Classification Search .................. 607/7, 8, 607/28
   See application file for complete search history.

(56) References Cited

U.S. PATENT DOCUMENTS

| | | | |
|---|---|---|---|
| 5,851,220 | A | 12/1998 | Murphy |
| 6,415,179 | B1 | 7/2002 | Pendekanti et al. |
| 6,859,664 | B2 | 2/2005 | Daum et al. |
| 6,889,077 | B2 | 5/2005 | Bornzin et al. |
| 6,904,314 | B1 | 6/2005 | Brewer et al. |
| 2002/0133206 | A1* | 9/2002 | Daum et al. ................. 607/14 |
| 2008/0249581 | A1* | 10/2008 | Wei ................................ 607/8 |

OTHER PUBLICATIONS

Zhou et al., "Epicardial mapping of ventricular defibrillation with monophasic and biphasic shocks in dogs," Circ Res vol. 72, No. 1, Jan. 1993, pp. 145-160.

Idriss et al., "Predicting the potential gradient field in ventricular fibrillation from shocks delivered in paced rhythm," Am J Physiol Heart Circ Physiol 268, 1995, pp. H2336-H2344.

Russo et al., "Defibrillation threshold testing: Is it really necessary at the time of implantable cardioverter-defibrillator insertion?" Heart Rhythm, vol. 2, No. 5, May 2005, pp. 456-461.

Chen et al., "the potential gradient field crated by epicardial defibrillation electrodes in dogs," Circulation, vol. 34, No. 3, Sep. 1986, pp. 626-636.

Macanu et al., "A comparison of biventricular and conventional transvenous defibrillation: A computation study using patient derived models," Pace, vol. 27, May 2004, pp. 586-593.

Pires et al., "intraoperative testing of the implantable cardioverter-defibrillator: How much is enough?," J Cardiovasc Electrophysiol, vol. 17, No. 2, Feb. 2006, pp. 140-145.

Sun et al., "DFT test via pacing measurements without VF induction and shocking," Abstract, Pace, vol. 23, p. 611.

* cited by examiner

*Primary Examiner* — Carl H. Rayno
*Assistant Examiner* — Tammie K Heller
(74) *Attorney, Agent, or Firm* — Steven M. Mitchell

(57) ABSTRACT

Systems and methods are provided for estimating a patient's ventricular defibrillation threshold (VDFT). Stimulation pulses, which are of at least three different energy levels up to 2 Joules, are delivered to the patient's right ventricle during a window defined between an R-wave and a vulnerable period that follows the R-wave. Voltage potentials, induced in response to the delivered RV stimulation pulses, are measured at a location of the patient's left ventricle (LV) where it is predicted that potential gradients induced in response to RV stimulation pulses will be lowest. Potential gradients are computed using the measured voltage potentials. The patient's VDFT can then be estimated by estimating, based on the computed potential gradients, the RV stimulation energy level that would be required to achieve a minimum acceptable potential gradient at the location of the patient's LV where it is predicted that potential gradients induced in response to RV stimulation pulses will be lowest.

25 Claims, 8 Drawing Sheets

VENTRICULAR DEFIBRILLATION THRESHOLD ESTIMATION

FIELD OF THE INVENTION

Embodiments of the present invention generally relate to implantable cardiac stimulation systems, and methods for use therewith. Specific embodiments relate to estimating a ventricular defibrillation threshold (VDFT).

BACKGROUND

A properly functioning human heart maintains its own intrinsic rhythm, and is capable of pumping adequate blood throughout the body's circulatory system. However, some people have irregular cardiac rhythms, referred to as cardiac arrhythmias. Such arrhythmias can result in diminished blood circulation. To treat such arrhythmias, cardiac stimulation devices can be implanted in a patient and used to deliver therapy to the patient's heart.

Such implantable stimulation devices can include pacemakers and/or defibrillators. Pacemakers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacemakers can be used, e.g., to treat patients with bradyarrhythmias, where a heart beats too slowly, or irregularly.

Defibrillators deliver higher energy electrical stimuli to the heart. Defibrillators can include cardioverters, which synchronize the delivery of the high energy electrical stimuli to portions of sensed intrinsic heart activity signals. Defibrillators can be used, e.g., to treat tachyarrhythmias, that is, where a hearts beat too quickly.

Tachyarrhythmias can cause diminished blood circulation because the heart doesn't have sufficient time to fill with blood before contracting to expel the blood. A defibrillator is capable of delivering a high energy electrical stimulus (often referred to as a shock), which interrupts the tachyarrhythmia, to thereby allow the heart to reestablish a normal sinus rhythm for the efficient pumping of blood.

Ventricular tachyarrhythmias, which originate in the ventricles, include ventricular tachycardia (VT) and ventricular fibrillation (VF). Ventricular arrhythmias are often associated with rapid and/or chaotic ventricular rhythms. For example, sustained ventricular tachycardia can lead to ventricular fibrillation. In sustained ventricular tachycardia, consecutive impulses arise from the ventricles at a rate of 100 bpm or more. Such activity may degenerate further into disorganized electrical activity known as ventricular fibrillation (VF). In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy, and asynchronous pacing may promote onset of ventricular arrhythmia. VF is typically fatal if not corrected within minutes.

A ventricular defibrillation threshold (VDFT) is the smallest amount of energy that can be delivered to the heart to reliably convert a ventricular fibrillation (VF) to a normal sinus rhythm. VDFTs vary from patient to patient, and may even vary within a patient depending on the placement of the electrodes used to deliver the therapy. In order to ensure the efficacy of such therapy and check device system integrity, the defibrillation threshold is preferably determined to ensure there is a large enough safety margin between the VDFT and a device's maximum shock capability. A large safety margin could prevent shock failure in case of increased VDFT caused by disease progression or the side effects of medication therapy. Determining VDFT could also provide information so that the defibrillation energy can be safely set above the threshold value but not at the device maximum capability, which might prolong device longevity and reduce the risk of fatal electro-mechanical dissociation caused by high energy shock.

Conventional techniques for determining VDFTs induce targeted tachyarrhythmias (e.g., ventricular fibrillations), and apply shocks of varying magnitude to determine the energy needed to convert arrhythmias into normal heart rhythms. However, such shocks can cause myocardial injury and hemodynamic instabilities. Further, such shocks are typically painful to the patient.

Since such conventional VDFT determination techniques subject patients to multiple VF episodes and high voltage shocks, exposing them to potentially detrimental effects of VF and applied shock, a patient's VDFT is often not determined. Alternatively, some physicians, mainly electrophysiologists, have used what is referred to as an abbreviated defibrillation safety margin (DSM) test, instead of the conventional VDFT test. However, with this abbreviated safety margin test, there is less certainty about the defibrillation efficacy of the selected shock strength.

A technique for estimating a patient's VDFT without applying defibrillation shocks or subjecting a patient to defibrillation has been proposed in U.S. Pat. No. 6,859,664, entitled "Cardiac Rhythm Management System with Defibrillation Threshold Prediction" (Daum et al.), which is incorporated herein by reference. In such technique, very low strength stimulation pulses (of less than 10 millijoules) are delivered to the patient's right ventricle (RV) using an RV coil electrode. A response is then measured between the RV coil electrode and an RV tip electrode, and between the RV tip electrode and the device housing, to thereby estimate the electric field distribution near the RV shock coil electrode. A distance from the RV shock electrode to the outer periphery of the left ventricular (LV) apex is also measured, e.g., using a fluoroscope or other imaging apparatus. Then, based on the estimate the electric field magnitude (also referred to as "potential gradient") near the RV shock electrode, and the measured distance from the RV shock electrode to the outer periphery of the left ventricular (LV) apex, a VDFT is estimated using a model of electric field distribution that provides a desired electric field magnitude (e.g., 5 Volts/cm) throughout the heart, including at its periphery.

While the VDFT estimation technique of the '664 patent does not subject a patient to fibrillation or high energy shocks, the inventors of the present invention question its accuracy. More specifically, the VDFT estimation of the '664 patent use potential gradient measurements in the RV, generalized potential gradient from passive electric field model, and distance measurements, to extrapolate what stimulation levels would be necessary to achieve a desired potential gradient (e.g., 5 Volts/cm) at the left ventricle (LV) epicardial surface near the apex, which is the least affected region in conventional transvenous defibrillation configuration. Such approximations introduce errors because they ignore another determinant of voltage gradient—the heterogeneity of cardiac tissue resistivity. Such errors can be significant in a diseased heart having malignant structural and functional heterogeneities. Moreover, the stimulations levels (≦10 V) used in the '664 patent are very far away from the actual voltage range of VDFT (150–830 V). Thus, the extrapolation of the '664 patent that uses passive models and relatively low stimulation levels may not be accurate enough to predict the VDFT.

Accordingly, there is a need for new techniques for estimating VDFTs. Preferably such techniques do not require the induction of ventricular fibrillation episodes.

SUMMARY

Embodiments of the present invention relate to systems and methods for estimating a patient's ventricular defibrillation threshold (VDFT). A plurality of stimulation pulses are delivered to the patient's right ventricle (RV), e.g., using an RV shock electrode. Such stimulation pulses, which are also referred to as low energy shocks, are of at least three different energy levels up to 2 Joules, and are preferably at least 10 millijoules. Each stimulation pulse is delivered during a window defined between an R-wave and a vulnerable period that follows the R-wave.

Voltage potentials, induced in response to the delivered RV stimulation pulses, are measured. In accordance with specific embodiments, such measurements occur at a location of the patient's left ventricle (LV) where it is predicted that potential gradients induced in response to RV stimulation pulses will be lowest, using three (non-linear) or more (non-planar) electrodes implanted at or near the location of the patient's LV. In accordance with specific embodiments, the location within the patient's LV, where it is predicted that potential gradients induced in response to RV stimulation pulses will be lowest, is the apex and/or posterior lateral wall of the patient's LV.

Potential gradients (induced in response to the delivered RV stimulation pulses) are computed using the measured voltage potentials. The patient's VDFT can then be estimated by estimating, based on the computed potential gradients, the RV stimulation energy level that would be required to achieve a minimum acceptable potential gradient at the location of the patient's LV where it is predicted that potential gradients induced in response to RV stimulation pulses will be lowest. This minimum acceptable potential gradient can be a potential gradient value (e.g., 5 Volts/cm) in the range of approximately 4 Volts/cm to approximately 6 Volts/cm.

Estimating the VDFT can include extrapolating, based on the computed potential gradients, a best fit line representative of the potential gradient at the location of the patient's LV as a function of RV stimulation energy levels. Then, there is an estimation, based on the extrapolated best fit line, of the RV stimulation level (measured in Joules or Volts) that is needed to achieve the minimum acceptable potential gradient at the location within the patient's LV where it is predicted that a potential gradient response to RV stimulation pulses will be lowest.

Embodiments of the present invention also relate to monitoring heart disease progression, based on changes in a patient's VDFT over time.

This summary is not intended to be a complete description of the invention. Other features and advantages of the invention will appear from the following description in which the preferred embodiments have been set forth in detail, in conjunction with the accompanying drawings and claims.

DETAILED DESCRIPTION

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed systems and methods, which are for estimating a ventricular defibrillation threshold (VDFT), are generally intended for use with an implantable cardiac stimulation device capable of detecting and treating arrhythmias. An exemplary implantable cardiac device will thus be described in conjunction with FIGS. 1 and 2. Additionally, FIGS. 3A and 3B will be used to describe an exemplary external programmer that can be used to program and control implantable cardiac stimulation devices, as well as upload information from implantable cardiac devices and analyze such information. It is recognized, however, that numerous variations of such devices exist, and that embodiments of the present invention can be implemented with such alternative device.

Figure 1:
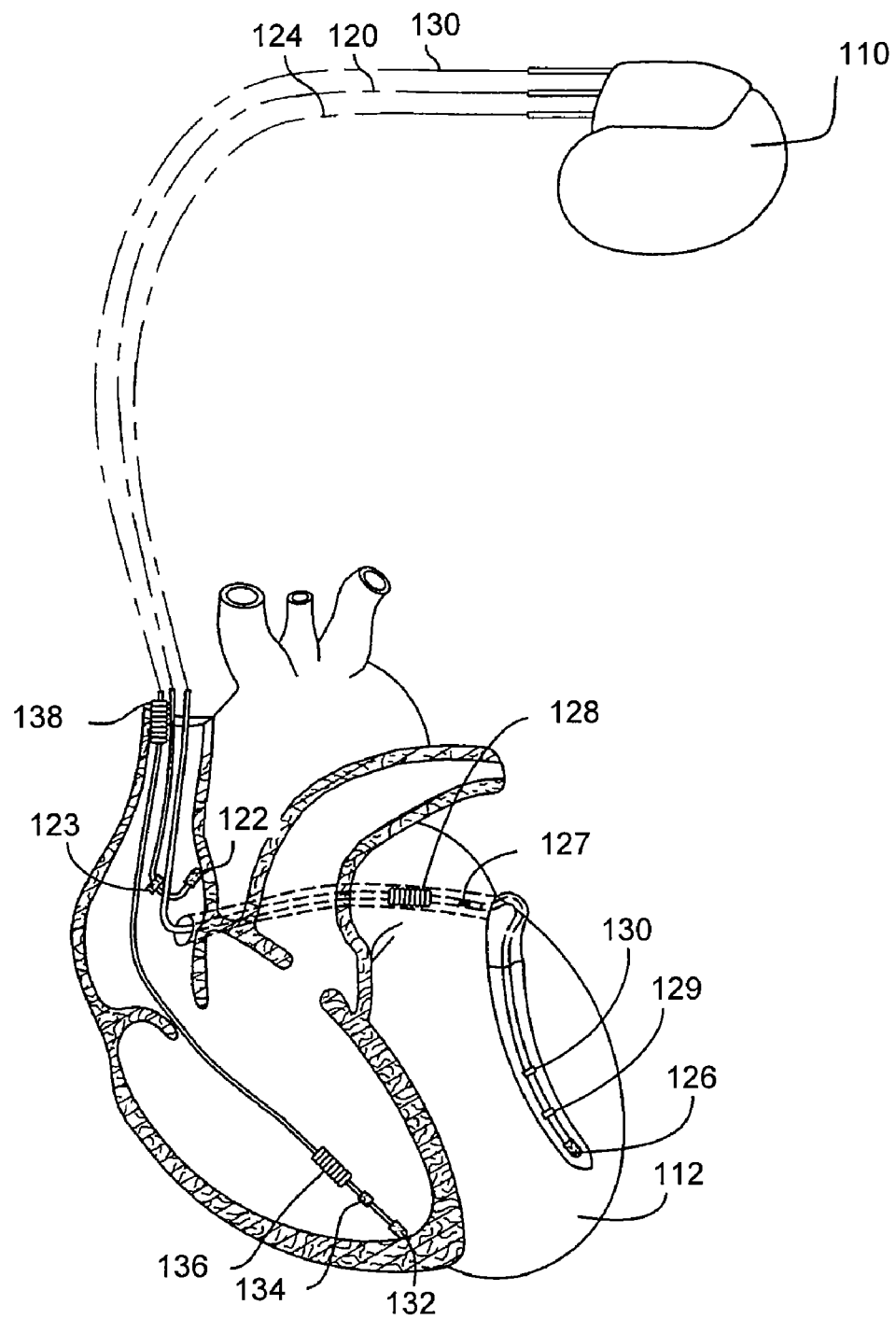
FIG. 1 is a simplified, partly cutaway view illustrating an exemplary implantable stimulation device in electrical communication with at least three leads implanted into a patient's heart for delivering multi-chamber stimulation and shock therapy.

Referring to FIG. 1, an exemplary implantable device 110 (also referred to as a pacing device, a pacing apparatus, a cardiac stimulation device, or simply a device) is in electrical communication with a patient's heart 112 by way of three leads, 120, 124 and 130, suitable for delivering multi-chamber stimulation. Preferably, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage, and a right atrial ring electrode 123. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The coronary sinus lead 124 is also shown as including two left ventricular ring electrodes 129 and 130.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
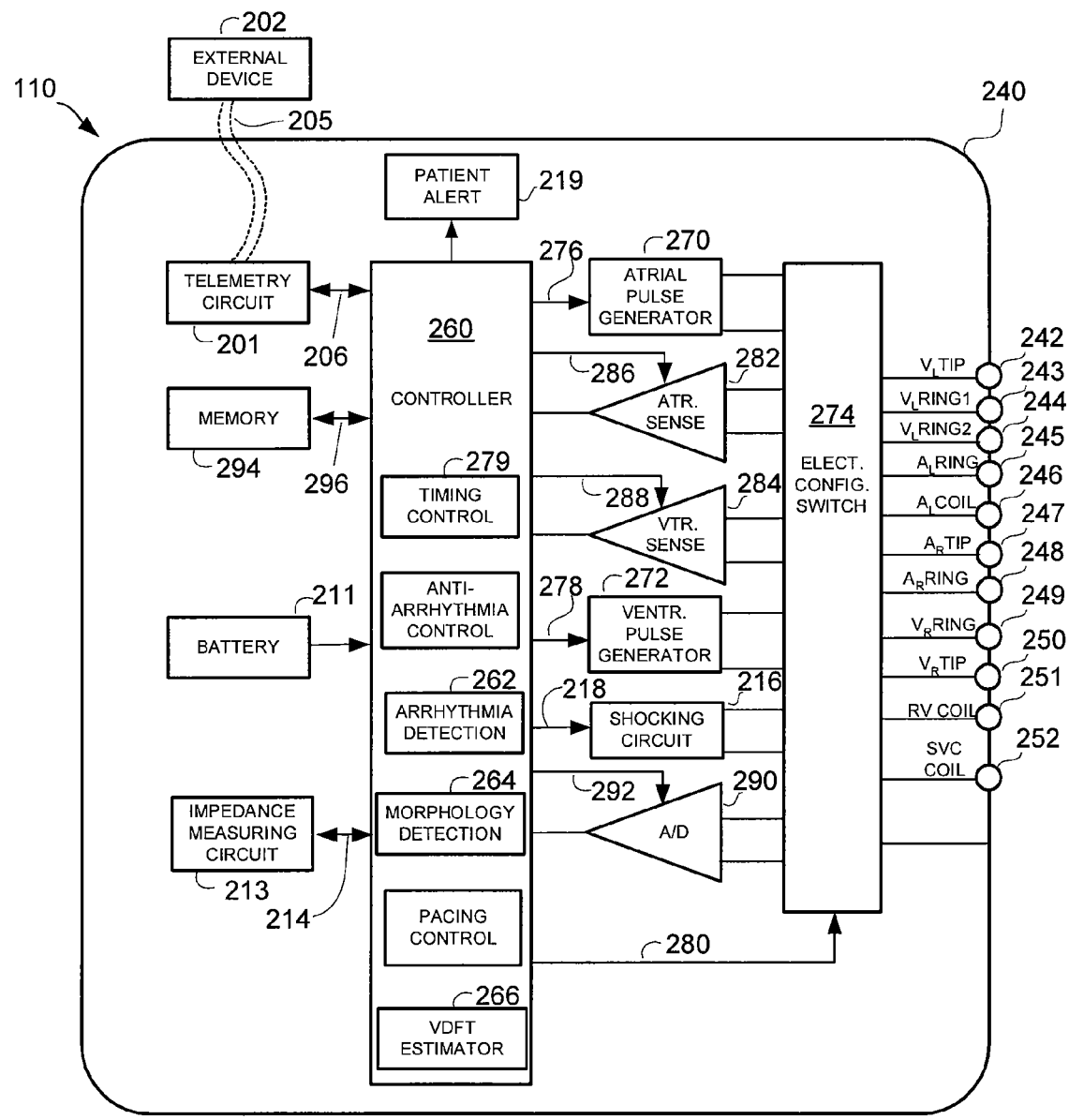
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242-252 (shown schematically and, for convenience, the names of the electrodes to which they are connected are shown next to the terminals). For example, to achieve right atrial sensing and pacing, the connector includes at least a right atrial tip terminal ($A_R$ TIP) 247 adapted for connection to the atrial tip electrode 122.

To achieve left atrial and ventricular sensing, pacing and shocking, the connector can include a left ventricular tip terminal ($V_L$ TIP) 242, a left atrial ring terminal ($A_L$ RING) 245, and a left atrial shocking terminal ($A_L$ COIL) 246, which are adapted for connection to the left ventricular tip electrode 126, the left atrial ring electrode 127, and the left atrial coil electrode 128, respectively.

To support right ventricle sensing, pacing and shocking, the connector further includes a right ventricular tip terminal ($V_R$ TIP) 250, a right ventricular ring terminal ($V_R$ RING) 249, a right ventricular shocking terminal ($R_V$ COIL) 251, and an SVC shocking terminal (SVC COIL) 252, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 includes an arrhythmia detector 262 and a morphology detector 264, that utilizes the atrial and ventricular sensing circuits, 282 and 284, to sense cardiac signals to determine whether a rhythm is physiologic or pathologic. The morphology detector 264 can, e.g., assess characteristics such as amplitude, area under curves, polarity, and shape, of detected cardiac rhythms.

The arrhythmia detector 264 can analyze the timing intervals between sensed events (e.g., P-waves, R-waves, and depolarization signals associated with fibrillation) and compare them to predefined rate zone limits (e.g., bradycardia, normal, low rate VT, high rate VT, and fibrillation rate zones), and various other characteristics such as morphology (as determined by the morphology detector 264) and/or sudden onset, stability, physiologic sensors, etc., in order to classify an arrhythmia, and thus, determine the type of remedial therapy that is needed (e.g., bradycardia pacing, anti-tachycardia pacing, cardioversion shocks or defibrillation shocks).

The arrhythmia detector 262 and/or morphology detector 264 can be implemented within the microcontroller 260, as shown in FIG. 2. Thus, the detectors 262 and/or 264 can be implemented by software, firmware, or combinations thereof. It is also possible that all, or portions, of the arrhythmia detector 262 and/or morphology detector 264 can be implemented using hardware. Further, it is also possible that all, or portions, of the detectors 262 and/or 264 can be implemented separate from the microcontroller 260. It is also possible that the features of the arrhythmia detector and morphology detector be incorporated into a single detector. These detectors can use discriminator parameters to assist in classifying arrhythmias. Values and uses of such parameters can be automatically adjusted in accordance with embodiments of the present invention, as described below.

Exemplary types of arrhythmias that the arrhythmia detector 262 can detect include, but are not limited to, SVT (e.g., AF), VT and VF. VF is a very fast (e.g., over 200 beats per minute) and chaotic heart rate in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF typically quickly becomes more erratic, often resulting in sudden cardiac arrest. This arrhythmia should be corrected immediately via a shock from an external defibrillator or an implantable cardioverter defibrillator (ICD). The defibrillator stops the chaotic electrical activity and restores normal heart rhythm. Embodiments of the present invention, through estimation of VDFT, can be used to estimate the energy levels of such shocks that are used to defibrillation a patient that is experiencing VF.

In accordance with embodiments of the present invention, the implantable device 110 can store, in memory 294, IEGM data corresponding to the period immediately prior to, during and subsequent to a detected arrhythmia. The implantable device can also store data that identifies the type of arrhythmia, the time of the arrhythmia (e.g., a time stamp), the duration of the arrhythmia, as well as any other type of information that a caregiver may deem useful. U.S. Pat. No. 4,295,474 (Fischell) and U.S. Pat. No. 5,732,708 (Nau et al.), each of which is incorporated herein by reference, provide exemplary additional details of the types of data that can be stored in response to the detection of an arrhythmia (and other cardiac events), and how such data can be efficiently and effectively stored.

Still referring to FIG. 2, cardiac signals are also applied to the inputs of an analog-to-digital (ND) data acquisition system 290. The data acquisition system 290 is configured to acquire intracardiac electrogram (IEGM) signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes. In specific embodiments, the data acquisition system 290 may be used to acquire IEGM signals for the analysis.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy.

The operating parameters of the implantable device 110 may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes one or more battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected. Certain embodiments of the present invention, as will be appreciated from the discussion further below, can be used to extend the life of a the battery 211 by reducing the quantity of high voltage shocks delivered.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

Because the implantable cardiac stimulation device 110 may operate as an implantable cardioverter defibrillator device, it should detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses, which can be used to estimate VDFT in accordance with embodiments of the present invention, as controlled by the microcontroller 260. Such shocking pulses are applied to the patient's heart 112 through at least two shocking electrodes, and as shown in this embodiment, selected from the left atrial coil electrode 128, the RV coil electrode 136, and/or the SVC coil electrode 138. As noted above, the housing 240 (also referred to as the housing electrode) may act as an active electrode in combination with the RV coil electrode 136, or as part of a split electrical vector using the SVC coil electrode 138 or the left atrial coil electrode 128 (i.e., using the RV electrode as a common electrode). Use of additional and/or alternative electrodes is also possible, as would be appreciated by one of ordinary skill in the art.

Also shown in FIG. 2 is a VDFT estimator 266, which can estimate values for VDFT, using techniques of the present invention. The VDFT estimator 266, which can be part of the controller 260, can be implemented in software, firmware, hardware, or combinations thereof. It is also possible that the VDFT estimator 266 be implemented outside the controller 260, or at least partially outside the controller 260.

The above described implantable device 110 was described as an exemplary device. One or ordinary skill in the art would understand that embodiments of the present invention can be used with alternative types of implantable devices. Accordingly, embodiments of the present invention should not be limited to use only with the above described device.

Figure 3A:
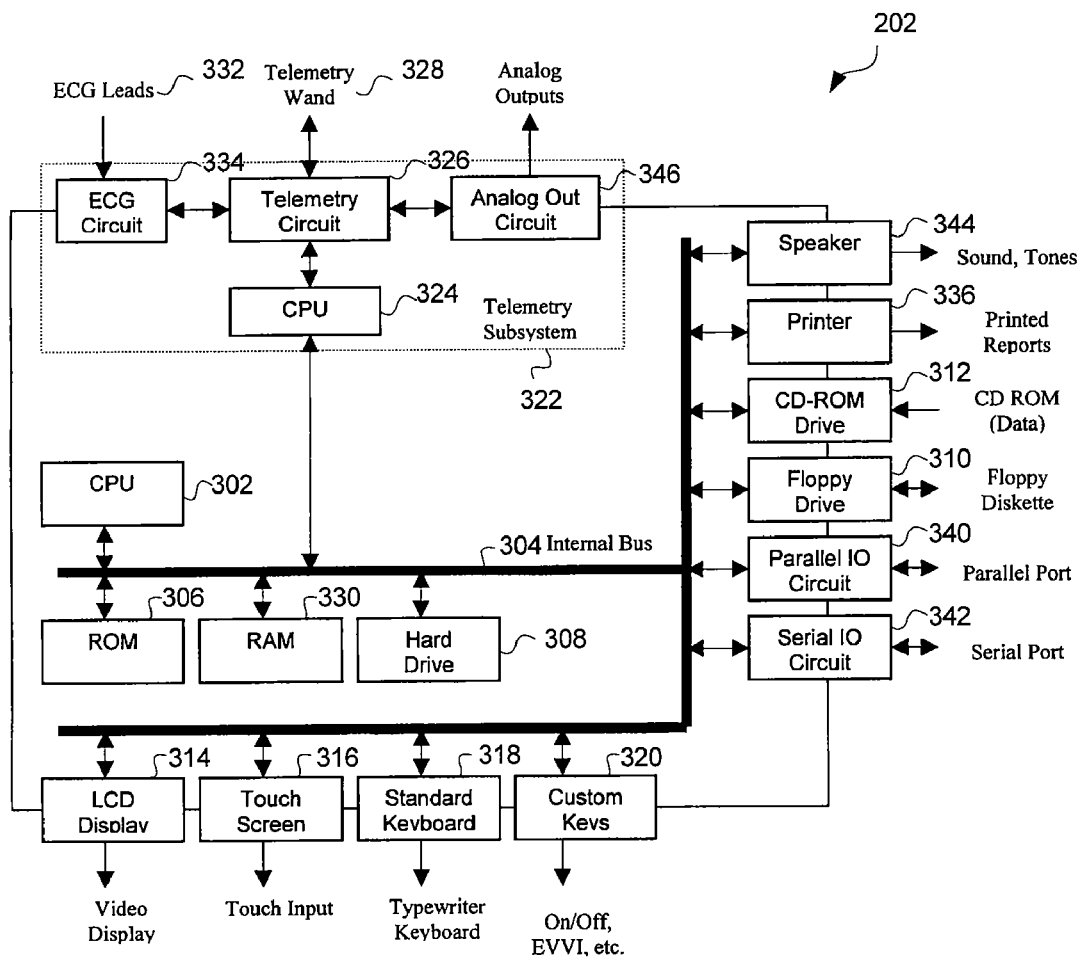
FIG. 3A is a functional block diagram of an exemplary external programmer device that can be used to program the implantable device of FIGS. 1 and 2, and to upload and analyze data collected by the implantable device.

FIG. 3A will now be used to illustrate components of an exemplary external programmer 202 for use in programming the implantable device 110, uploading data from the implantable device, and analyzing such data. Briefly, the programmer permits a physician or other caregiver to program the operation of the implantable device 110 and to retrieve and display information received from the implantable device such as IEGM data and device diagnostic data. Additionally, the external programmer can receive and display EKG data from separate external EKG leads that may be attached to the patient. As will be described in further detail below, in accordance with embodiments of the present invention, the external programmer 202 is capable of processing and analyzing data received from the implantable device 110.

Operations of the programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU 302 displays a menu of programming options to the user via an LCD display 314 or other suitable computer display device. To this end, the CPU may, for example, display a menu of specific programming parameters of the implantable device to be programmed or may display a menu of types of diagnostic data to be retrieved and displayed. In response thereto, the caregiver enters various commands via either a touch screen 316 overlaid on the LCD display or through a standard keyboard 318 supplemented by additional custom keys 320, such as an emergency VVI (EVVI) key. The EVVI key sets the implantable device to a safe VVI mode with high pacing outputs. This ensures life sustaining pacing operation in nearly all situations but by no means is it desirable to leave the implantable device in the EVVI mode at all times. These are just a few examples of the types of user interfaces of the programmer, which are not meant to be limiting. Inclusion and use of other types of user interfaces are possible, and within the scope of the present invention.

Once all pacing leads are mounted and the implantable device 110 is implanted, the various devices are programmed. Typically, the caregiver initially controls the programmer 202 to retrieve data stored within any implantable device 110 and to also retrieve EKG data from EKG leads 332, if any, coupled to the patient. To this end, the CPU 302 transmits appropriate signals to a telemetry subsystem 322, which provides components for directly interfacing with the implantable device 110, and the EKG leads. Telemetry subsystem 322 includes its own separate CPU 324 for coordinating the operations of the telemetry subsystem. Main CPU 302 of programmer communicates with telemetry subsystem CPU 324 via internal bus 304. Telemetry subsystem 322 additionally includes a telemetry circuit 326 connected to telemetry wand 328, which, in turn, receives and transmits signals electromagnetically from the telemetry unit 201 of the implantable device 110. The telemetry wand 328 is placed over the chest of the patient near the implantable device to permit reliable transmission of data between the telemetry wand 328 and the implantable device 110.

Typically, at the beginning of the programming session, the external programming device 202 controls the implantable device 110 via appropriate signals generated by the telemetry wand 328 to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implantable device such as lead impedances, battery voltages, battery recommended replacement time (RRT) information and the like. Data retrieved from the implantable device 110 is stored by external programmer 202, e.g., within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable device 110 is transferred to programmer 202, the implantable device 110 may be further controlled to transmit additional data in real time as it is detected by the implantable device 110, such as additional IEGM data, lead impedance data, and the like.

As will be explained in more detail below, in specific embodiments of the present invention the programmer 202 can instruct the device 110 to perform certain functions that enable a VDFT to be estimated. The actual computations that are used to estimate a VDFT can be performed within the programmer 202, within the implantable device 110, or within both devices. In other words, there can be distributed processing of such computations. When it is the programmer 202 that determines an initial (or updated) VDFT estimation, the value of such a VDFT estimation can be provided from the programmer 202 to the device 110 using the telemetry subsystem 322.

It is also possible that the telemetry subsystem 322 receives EKG signals from EKG leads 332 via an EKG processing circuit 334. As with data retrieved from the implantable device itself, signals received from the EKG leads can be stored within one or more of the storage devices of the external programmer. Typically, EKG leads output analog electrical signals representative of the EKG. Accordingly, EKG circuit 334 includes analog to digital conversion circuitry for converting the signals to digital data appropriate for further processing within programmer. Depending upon the implementation, the EKG circuit 334 may be configured to convert the analog signals into event record data for ease of processing along with the event record data retrieved from the implantable device. Typically, signals received from the EKG leads are received and processed in real time. Thus, the programmer 202 can receive data both from the implantable device 110 and from the external EKG leads 332.

Data retrieved from the implantable device 110 includes parameters representative of the current programming state of the implantable device 110. Under the control of the caregiver, the external programmer 202 displays the current programming parameters and permits the caregiver to reprogram the parameters. To this end, the caregiver enters appropriate commands via any of the aforementioned input devices and, under control of CPU 302, the programming commands are converted to specific programming parameters for transmission to the implantable device 110 via telemetry wand 328 to thereby reprogram the implantable device 110. A wide variety of parameters may be programmed by the caregiver, including, but not limited to atrioventricular and inter-ventricular delay values. Prior to reprogramming specific parameters, the caregiver may control the external programmer 202 to display any or all of the data retrieved from the implantable device 110 or from the EKG leads, including displays of ECGs, IEGMs, and statistical patient information. Any or all of the information displayed by programmer may also be printed using a printer 336.

The programmer 202 can also include a modem (not shown) to permit direct transmission of data to other programmers via the public switched telephone network (PSTN) or other interconnection line, such as a T1 line or fiber optic cable. Depending upon the implementation, the modem may be connected directly to internal bus 304 may be connected to the internal bus via either a parallel port 340 or a serial port 342. Other peripheral devices may be connected to the external programmer via parallel port 340 or a serial port 342 as well. Although one of each is shown, a plurality of input output (IO) ports might be provided. A speaker 344 is included for providing audible tones to the user, such as a warning beep in the event improper input is provided by the caregiver. The telemetry subsystem 322 additionally includes an analog output circuit 346 for controlling the transmission of analog output signals, such as IEGM signals output to an EKG machine or chart recorder.

With the programmer 202 configured as shown, a physician or other caregiver operating the external programmer 202 is capable of retrieving, processing and displaying a wide range of information received from the EKG leads or from the implantable device 110 and to initially program and/or to reprogram the implantable device 110 if needed. The descriptions provided herein with respect to FIG. 3A are intended merely to provide an overview of the operation of an exemplary external programmer 202 and are not intended to describe in detail every feature of the hardware and software of the device and is not intended to provide an exhaustive list of the functions performed by the device.

The programmer 202 can include software, firmware, hardware, or combinations thereof, that can control the algorithms or assist with the algorithms for estimating VDFTs, in accordance with embodiments of the present invention. For example, the programmer 202 can instruct the implanted device 110 to perform certain steps discussed below. The programmer can also perform steps (or parts thereof) that may require extensive processing, such as line fitting, or the like. Alternatively, the implanted device 110 can perform all or a majority of such steps.

Figure 3B:
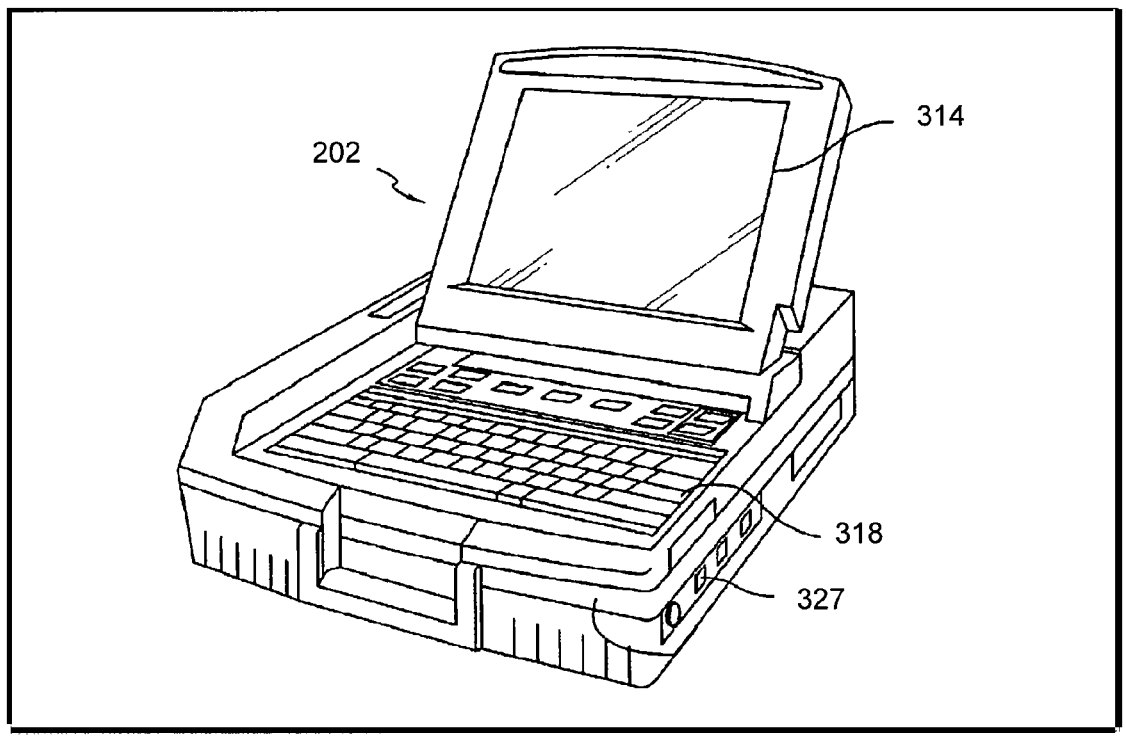
FIG. 3B is an exemplary perspective view of the exemplary external programmer device of FIG. 3A.

FIG. 3B is an exemplary perspective view of the exemplary programmer 202 introduced in FIG. 3A. Referring to FIG. 3B, the programmer 202 is shown as including a display 314, a keyboard 318, and a connector 327 for accepting a cable of a telemetry wand (328 in FIG. 3A).

As mentioned above, embodiments of the present invention are directed to systems and methods for estimating a patient's ventricular defibrillation threshold (VDFT). Such systems can be implemented, e.g., as implantable cardiac stimulation devices (e.g., 110), external programmers (e.g., 202), or combinations thereof. The methods of the present invention can be performed, e.g., by such systems.

Embodiments can provide physicians with an automated VDFT estimation tool, that does not require VF induction and high energy shock, can reduce implant time, potentially prolong device longevity (by saving power), and reduce and preferably eliminate risks to patients at implant test. Such an automated tool, as will be described below, can be used to estimates VDFTs by delivering programmed low voltage/low energy stimulation.

Figure 4:
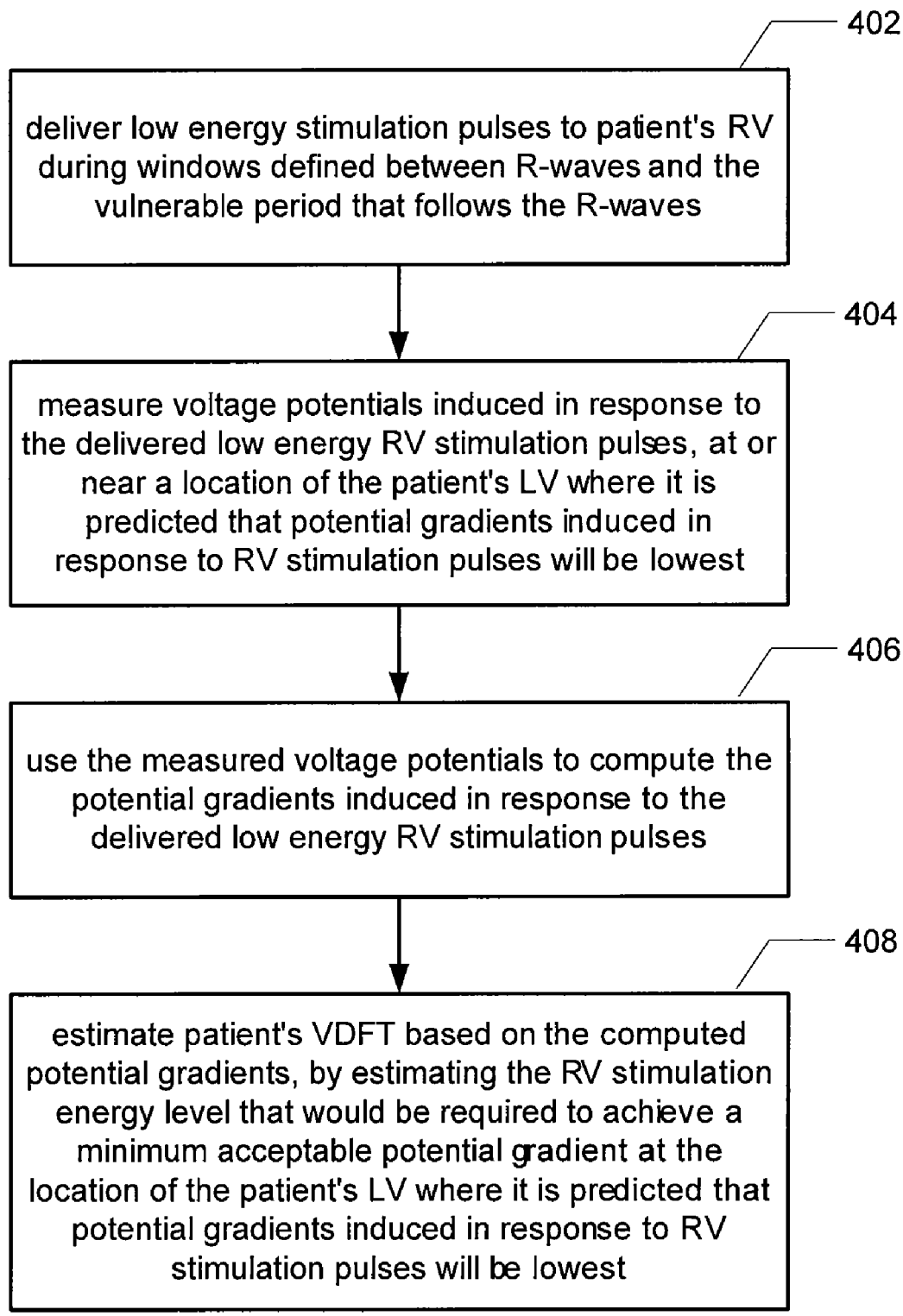
FIG. 4 is a high level flow diagram that is used to summarize embodiments of the present invention.
Figure 5:
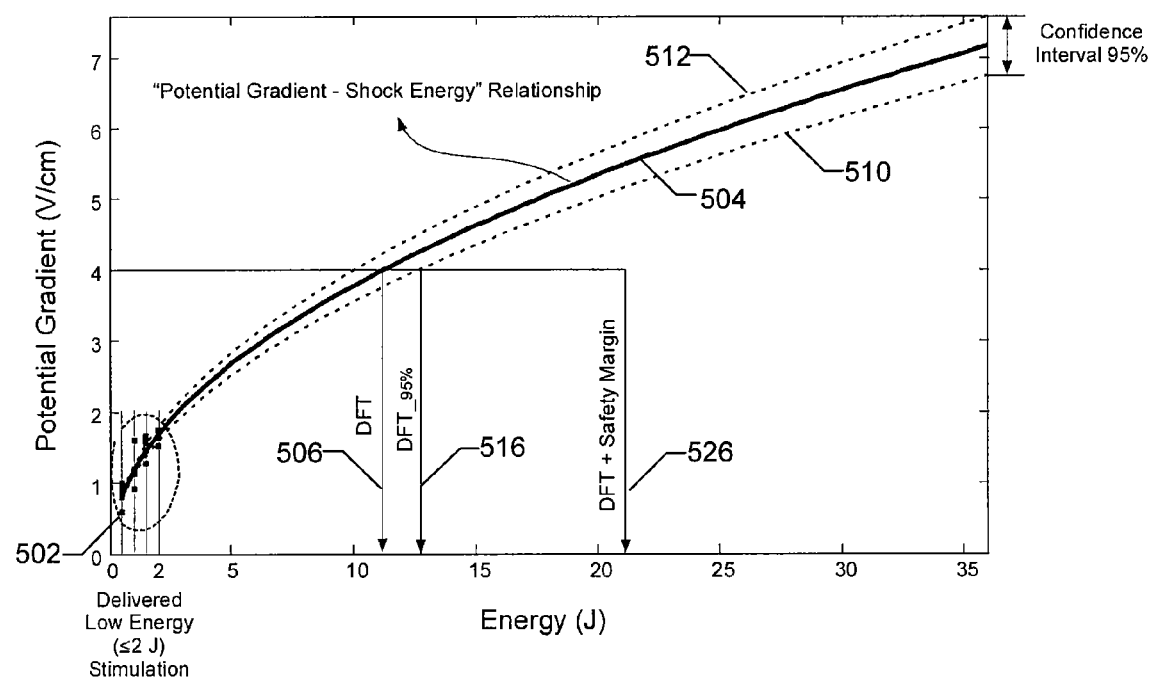
FIG. 5 is a graph that shows how a ventricular defibrillation threshold can be estimated by extrapolating a best fit line based on computed potential gradients.

Embodiments of the present invention will now be summarized with reference to the high level flow diagram of FIG. 4, and the graph of FIG. 5. Referring to FIG. 4, at a step 402, a plurality of stimulation pulses are delivered to a patient's right ventricle (RV). The stimulation pulses are preferably of at least three different energy levels up to, but not exceeding, 2 Joules. It is preferred that 2 Joules not be exceeded, because pulses exceeding 2 Joules can potentially be intolerable to the patient, whereas pulses not exceeding 2 Joules are rarely felt by the patient and they generally do not induce myocardial damage. The stimulation pulses delivered at step 402 are also referred to as low energy shocks. As will be described below, the responses to such low energy shocks are used to estimate VDFT. Such low energy shocks, the responses to which VDFT estimates are based, are of higher energy levels than pacing pulses. More specifically, it is preferred that the low energy shocks be of at least 10 millijoules, because response to energy levels lower than 10 millijoules are not believed to very useful in estimating VDFT due to the low signal amplitude and electrode impedance dynamics. In summary, it is preferred that the stimulation pulses delivered by the patient's RV at step 402 are greater than 10 millijoules, but not greater than 2 Joules. A shocking circuit (e.g., 216) can be used to generate such low energy shocks. The electrodes that are used to deliver these low energy shocks are preferably the same electrodes that will be used to deliver high energy shocks, should the patient need to be defibrillated in response to VF. For example, the RV shock electrode 136, SVC shock electrode 138, and the housing electrode 240 can be used at this step.

Additionally, in specific embodiments of the present invention, each stimulation pulse (whose response is used to estimate VDFT) is delivered during a window defined between an R-wave and a vulnerable period that follows the R-wave. A benefit of delivering the stimulation pulses outside the vulnerable period (also known as the vulnerable window), is it reduces the chance of inducing an arrhythmia. A benefit of delivering the stimulation pulses between an R-wave and the vulnerable period that follows the R-wave, is that the geometry and volume of the heart during this window is believed to be closer to the geometry and volume of the heart when the heart is experiencing VF, as compared to the invulnerable period during the diastolic phase. Thus, it is believed that cardiac responses during this window will provide for good estimates of VDFT.

The vulnerability period can be detected in various known manners. Alternatively, and more simply, each stimulation pulse can be delivered within (or at) 40 msec after the peak of the R-wave, which should ensure that delivery is prior to the vulnerability period.

Still referring to FIG. 4, at a step 404, voltage potentials induced in response to the delivered low energy RV stimulation pulses are measured at or near a location of the patient's left ventricle (LV) where it is predicted that potential gradients induced in response to RV stimulation pulses will be lowest. Such voltage potentials are measured using a sensing circuit (e.g., 284) and three (non-linear) or more (non-planar) electrodes implanted at or near the location of the patient's LV where it is predicted that potential gradients induced in response to RV stimulation pulses will be lowest. Such location can be the apex and/or posterior lateral wall of the patient's LV. Such electrodes can be located on a same interpericardial lead, located on a same transvenous lead, or even part of different leads. At a step 406, the measured voltage potentials are used to compute the potential gradients induced in response to the delivered low energy RV stimulation pulses.

Examples of computed potential gradients are shown at 502, in FIG. 5. A potential gradient is the local space rate of change of a voltage potential. A magnitude of a potential gradient can be computed, e.g., from peak voltages detected at a pair of electrodes and the inter-electrode distance between the pair of electrodes. Voltage potentials are measured between pairs of electrodes. The distances between such electrodes should be known so that potential gradients can be computed. Where electrodes are part of a same lead, it is easy to know the distance between such electrodes. Where electrodes are not part of a same lead, distances between electrodes can be measured using imaging, such as, but not limited to, fluoroscopy.

A potential vector can include x,y,z vectors, and the "potential gradient" can be the root mean square of the gradient amplitudes in x,y,z vectors. Whatever electrode arrangement that can record components in x,y,z direction can be used. Is it even possible to ignore one direction for simplification in electrode design, as is suggested in an article by Idriss et al entitled "Predicting the potential gradient field in ventricular fibrillation from shocks delivered in paced rhythm," *Am J Physiol Heart Circ Physiol* 268: H2336-H2344, 1995, which is incorporated herein by reference. Two electrodes can be used to compute the potential gradient in a line, which is a one-dimensional potential gradient. Three electrodes (that form a triangle) can be used to compute the potential gradient in a plane (e.g. x-y), which is a two-dimensional potential gradient. Four or more electrodes, in a non single plane arrangement, can be used to compute a three-dimensional potential gradient. Embodiments of the present invention cover all such possibilities. Some additional details on how to compute a two-dimensional potential gradient are provided in the Idress et al article that is incorporated herein by reference above.

At a step 408, the patient's VDFT is estimated based on the computed potential gradients, by estimating the RV stimulation energy level that would be required to achieve a minimum acceptable potential gradient at the location of the patient's LV where it is predicted that potential gradients induced in response to RV stimulation pulses will be lowest. The minimum acceptable potential gradient at the location within the patient's LV (where it is predicted that a potential gradient response to RV stimulation pulses will be lowest) can be a potential gradient value in the range of approximately 4 Volts/cm to approximately 6 Volts/cm.

Studies have shown that defibrillation shocks should generate a minimum potential gradient of approximately 4 V/cm (for typical biphasic waveforms) throughout the ventricles in order to succeed in defibrillation. Accordingly, in specific embodiments, the minimum acceptable potential gradient is approximately 4 V/cm. Therefore, in specific embodiments the patient's VDFT is estimated by estimating the RV stimulation energy level that would be required to achieve a 4 V/cm potential gradient at the location of the patient's LV where it is predicted that potential gradients induced in response to RV stimulation pulses will be lowest. In other embodiments, where there is a desire to provide for more of a safety margin, the minimum potential gradient is approximately 5 V/cm. Use of other minimum potential gradients are possible, and also within the scope of embodiments of the present invention.

As mentioned above, the minimum potential gradient should be achieved throughout the ventricles, in order to succeed in defibrillation. This means that even at the location where the potential gradient is the lowest in response to RV stimulation pulses, the minimum potential gradient should be achieved. In response to RV stimulation pulses, the potential gradients in the LV will be lower than potential gradients in the RV. Even more specifically, it is expected that the potential gradient response to the RV stimulation pulses will be lowest at the apex or posterior lateral wall of the patient's LV. Thus, to successfully defibrillate the patient, it is believed that the potential gradient response at the apex and posterior lateral wall of the patient's LV should reach the minimum potential gradient. This is why, at step 404, the induced voltage potentials are measured at or near the location of the patient's LV where it is predicted that potential gradients induced in response to RV stimulation pulses will be lowest.

Some prior suggested techniques for estimating DFTs, such as that described in an article by Zhou et al, entitled "Epicardial mapping of ventricular defibrillation with monophasic and biphasic shocks in dogs," Circulation Research, Vol. 72, No. 1, pp 145-160, January 1993, discuss measuring voltage potentials at over 100 locations using over 100 electrodes. Such techniques would not be practical for use with a device that is chronically implanted in a human. Rather, in accordance with specific embodiments of the present invention, voltage potentials (induced in response to the low energy RV stimulation pulses) are only measured at the location of the patient's LV where it is predicted that potential gradients induced in response to RV stimulation pulses will be lowest. This is more practical, because it can be accomplished with as few as three electrodes, but more electrodes (e.g., four or more) can be used if desired.

The estimation performed at step 408 can be achieved by extrapolating, based on the computed potential gradients, a best fit line representative of the potential gradient at the location of the patient's LV as a function of RV stimulation energy levels. Such a best fit line should extend to at least the minimum acceptable potential gradient. Then, based on the extrapolated best fit line, the VDFT can be estimated as the RV stimulation energy level that is needed to achieve the minimum acceptable potential gradient at the location within the patient's LV where it is predicted that a potential gradient response to RV stimulation pulses will be lowest. For example, nonlinear or linear least squares data fitting can be used to perform such extrapolation. Exemplary algorithms that can be used to provide such extrapolation include, but are not limited to, Levenberg-Marquardt, Gauss-Newton and gradient descent.

FIG. 5 illustrates an exemplary best fit line 504 that can be extrapolated based on computed potential gradients produced at step 406. In FIG. 5 it is presumed that the minimum acceptable potential gradient is 4 V/cm. In the example of FIG. 5, the estimated energy required to achieve a 4 V/cm potential gradient is shown as being approximately 11 Joules, as indicated by line 506. Thus, for the example of FIG. 5, the estimated VDFT is 11 Joules. In additional to fitting a line (e.g., 504) to the computed potential gradients that correspond to the low energy ($\leq 2$ Joules) stimulation pulses, global confidence bands 510 and 512 can also be extrapolated to the high energy range, e.g., until it reaches the upper limit of stored energy of the device. In FIG. 5, the confidence bands 510 and 512 are 95% confidence bands, but lower or higher percentage confidence bands can be used. Such confidence bands 510 and 512 can be used to provide a more conservative VDFT estimate. More specifically, referring to FIG. 5, the 95% confidence band 510 can be used to determine a conservative VDFT estimate of approximately 12.5 Joules, as indicated by line 516. The actual shock energy used to defibrillate a patient, e.g., in response to detecting VF, can be set to be the VDFT estimate (approximately 11 Joules), the conservative VDFT estimate (approximately 12.5 Joules), or one of those estimates plus a specified safety margin, as indicated by line 526. Such a safety margin (which can be added to the VDFT or conservative VDFT) can be a fixed value (e.g., 10 Joules), or a percentage (e.g., 90% of the VDFT), or the like.

In specific embodiments, at step 402 the patient's heart is paced with what shall be referred to as a S1-S2 pattern, where S1 is a regular pacing pulse delivered (e.g., to the RV apex), and S2 is a low energy shock (>10 millijoules and $\leq 2$ J). By randomizing delivery of multiple low energy shocks at precise intervals with respect to the preceding pacing pulse, the algorithm estimates the "potential gradient—shock energy" relationship. The S1-S2 pattern allows for synchronizing each low energy shock to a pacing pulse such that the vulnerable window is avoided, and there is substantially no risk of arrhythmogenesis.

Figure 6:
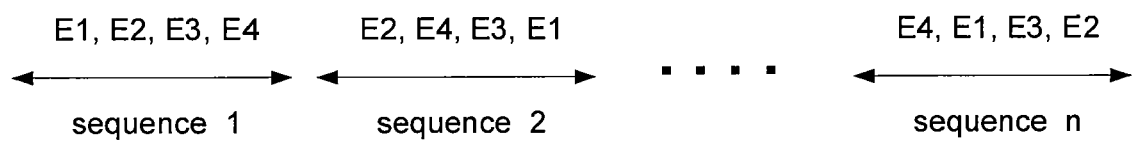
FIG. 6 illustrates an exemplary protocol that can be used to deliver the low energy shocks, the response to which is measured and used to estimate a ventricular defibrillation threshold, in accordance with embodiments of the present invention.

FIG. 6 illustrates an exemplary protocol for the delivery of low energy shocks at consecutive beats (at step 402). In this example, assume the low energy shocks E1, E2, E3 and E4 have energy levels of 0.5 J, 1.0 J, 1.5 J, and 2 J, respectively. Such stimulation pulses can be biphasic pulses, or monophasic pulses, although biphasic are preferred. Each biphasic pulse includes two phases, each of which has a slew rate, duration and amplitude, which may be common of differ between the two phases. These low energy shocks can be synchronized to the pacing pulses, and delivered at the early plateau phase of an action potential to avoid VF induction. More generally, the low energy shocks are preferably delivered during the window defined between an R-wave and the vulnerable period that follows the R-wave, for reasons discussed above.

The voltage potential induced by each low energy shock can be recorded by using sensing electrodes, enabling the potential gradient caused by each low energy shock to be computed. In specific embodiments, for conventional transvenous defibrillation, sensing electrodes can be positioned close to LV apex intravenously through the coronary veins or subcutaneously. In specific embodiments, for other defibrillation configurations (e.g. defibrillation with additional epicardial or subcutaneous patch, or biventricular transvenous defibrillation), sensing electrodes can be positioned to the posterior LV base intravenously through the coronary sinus.

In specific embodiments, the various (four in this example) low energy shocks can be repeatedly delivered in order to get multiple measurements for each energy level. Averages can be determined from the multiple measurements, which should increase the accuracy of the VDFT estimation. In other words, at step 402, multiple RV stimulation pulses can be delivered at each of the at least three different energy levels. At step 404, for each of the different RV stimulation energy levels, an average of the induced voltage potential measurements can be produced for each of the different low energy shock levels. In specific embodiments, each time the sequence is repeated, the order of the sequence of the low energy shocks are randomized, as can be appreciated from FIG. 6.

It is also possible to test more than one low energy shock during a same heart beat, which may further reduce the testing duration. In other words, more than one low energy shock can be delivered between a pair of consecutive R-waves, and more specifically, between an R-wave and the vulnerability period that follows the R-wave.

The above described embodiments of the present invention can be performed autonomously by an implanted cardiac stimulation device, or by an implanted cardiac stimulation device that is being controlled by an external programmer. Such an external programmer (e.g., 202), an example of which is discussed above, wirelessly communicates with the implanted cardiac stimulation device (e.g., 110).

Figure 7:
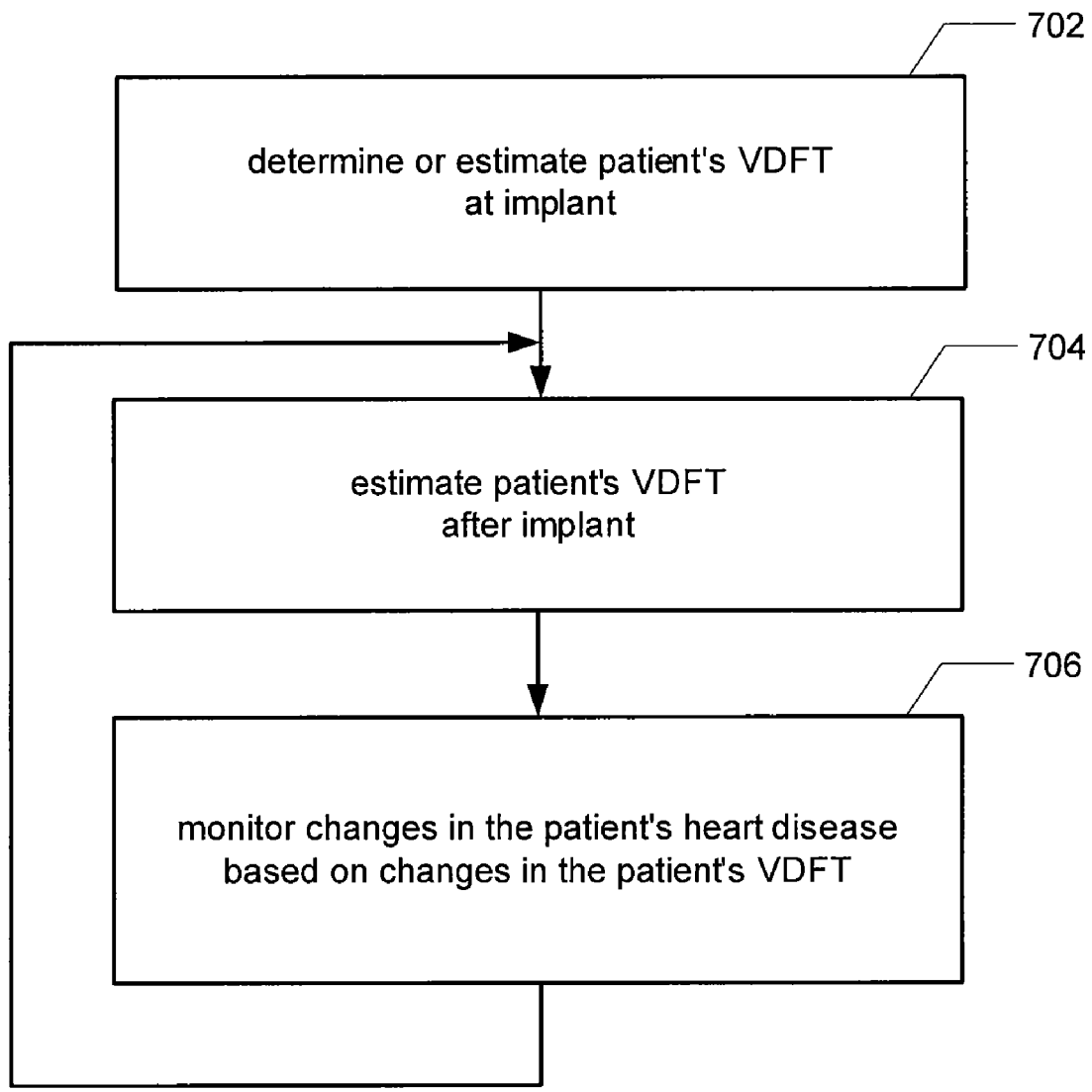
FIG. 7 is a high level flow diagram that is used to summarize embodiments of the present invention where heart disease progression is monitored based on estimates of the patient's ventricular defibrillation threshold.

The above described embodiments of the present invention can be used to estimate VDFT at the time of implantation of a cardiac stimulation device, and/or some time thereafter. In specific embodiments, a new estimate of VDFT is automatically determined from time to time (e.g., periodically, or aperiodically in response to a trigger) by an implanted device and/or an external programmer so that such estimates can be updated and/or to monitor if there is a change in the defibrillation efficacy after implant, and/or disease progression. More specifically, if estimates for VDFT increase over time, then there is a decrease in defibrillation efficacy, and vice versa. Also, an increase in estimated VDFT can be interpreted as a progression (worsening) in a heart disease that affects heart size, conductivity or heterogeneity, and vice versa. This is summarized in steps 702-706 of the high level flow diagram of FIG. 7.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for estimating a patient's ventricular defibrillation threshold (VDFT), comprising:
  (a) delivering a plurality of stimulation pulses to the patient's right ventricle (RV), the stimulation pulses being of at least three different energy levels up to 2 Joules, wherein each said stimulation pulse is delivered during a window defined between an R-wave and a vulnerable period that follows the R-wave;
  (b) measuring voltage potentials induced in response to the RV stimulation pulses delivered at step (a), at or near a location of the patient's left ventricle (LV) where it is predicted that potential gradients induced in response to RV stimulation pulses will be lowest, wherein the voltage potentials are measured between one or more pairs of electrodes of a plurality of electrodes implanted at or near the location of the patient's LV where it is predicted that potential gradients induced in response to RV stimulation pulses will be lowest;
  (c) using the voltage potentials measured at step (b) to compute the potential gradients, induced in response to the RV stimulation pulses delivered at step (a), for the location of the patient's LV where it is predicted that potential gradients induced in response to RV stimulation pulses will be lowest; and
  (d) estimating the patient's VDFT by estimating, based on the potential gradients computed at step (c), the RV stimulation energy level that would be required to achieve a minimum acceptable potential gradient at the location of the patient's LV where it is predicted that potential gradients induced in response to RV stimulation pulses will be lowest;
  wherein the location within the patient's LV, where it is predicted that potential gradients induced in response to RV stimulation pulses will be lowest, is the apex and/or posterior lateral wall of the patient's LV.

2. The method of claim 1, wherein the voltage potentials induced in response to the RV stimulation pulses are only measured at or near the location of the patient's left ventricle (LV) where it is predicted that potential gradients induced in response to RV stimulation pulses will be lowest.

3. The method of claim 2, wherein at least two of the plurality of electrodes, implanted at or near the location of the patient's LV, are part of a same intrapericardial left ventricular lead.

4. The method of claim 2, wherein at least two of the plurality of electrodes, implanted at or near the location of the patient's LV, are part of a same coronary sinus transvenous left ventricular lead.

5. The method of claim 2, wherein at least one of the plurality of electrodes, implanted at or near the location of the patient's LV, is part of a different lead than another one of the electrodes.

6. The method of claim 1, wherein the minimum acceptable potential gradient at or near the location of the patient's LV, where it is predicted that a potential gradient response to RV stimulation pulses will be lowest, is a potential gradient value in the range of approximately 4 Volts/cm to approximately 6 Volts/cm.

7. The method of claim 1, wherein:
step (a) includes delivering multiple RV stimulation pulses at each of the at least three different energy levels; and
step (b) includes determining, for each of the different RV stimulation energy levels, an average of the voltage potentials measured at or near the location of the patient's LV where it is predicted that potential gradients induced in response to RV stimulation pulses will be lowest.

8. The method of claim 1, wherein step (d) includes:
(d.1) extrapolating, based on the potential gradients computed at step (c), a best fit line representative of the potential gradient at or near the location of the patient's LV as a function of RV stimulation energy levels, where the best fit line extends to at least the minimum acceptable potential gradient; and
(d.2) estimating, based on the extrapolated best fit line, the RV stimulation energy level that is needed to achieve the minimum acceptable potential gradient at the location within the patient's LV where it is predicted that a potential gradient response to RV stimulation pulses will be lowest.

9. The method of claim 1, wherein:
the stimulation pulses delivered in step (a) are biphasic pulses.

10. The method of claim 1, wherein at least three of the different energy levels used at step (a) are greater than 10 millijoules, but not greater than 2 Joules.

11. The method of claim 1, wherein the energy level of one or more of the of the plurality of stimulation pulses delivered to the patient's RV at step (a) is/are between 1 and 2 Joules.

12. A system for estimating a patient's ventricular defibrillation threshold (VDFT), comprising:
a plurality of implanted electrodes, at least two of which can be used to deliver stimulation and at least two of which can be used to sense responses to delivered stimulation;
a shocking circuit to deliver a plurality of stimulation pulses to the patient's right ventricle (RV), using at least two of the electrodes, the stimulation pulses being of at least three different energy levels up to 2 Joules, wherein each said stimulation pulse is delivered during a window defined between an R-wave and a vulnerable period that follows the R-wave;
a sensing circuit to measure voltage potentials induced in response to the delivered RV stimulation pulses, at a location of the patient's left ventricle (LV) where it is predicted that potential gradients induced in response to RV stimulation pulses will be lowest, using three or more electrodes of the plurality of implanted electrodes, wherein the three or more electrodes are implanted at or near the location of the patient's LV where it is predicted that potential gradients induced in response to RV stimulation pulses will be lowest;
one or more processors to
compute the potential gradients induced in response to the delivered RV stimulation pulses based on the measured voltage potentials, wherein the computed potential gradients are for the location of the patient's LV where it is predicted that potential gradients induced in response to RV stimulation pulses will be lowest, and
estimate the patient's VDFT by estimating, based on the computed potential gradients, the RV stimulation energy level that would be required to achieve a minimum acceptable potential gradient at the location of the patient's LV where it is predicted that potential gradients induced in response to RV stimulation pulses will be lowest;
wherein the location within the patient's LV, where it is predicted that potential gradients induced in response to RV stimulation pulses will be lowest, is the apex and/or posterior lateral wall of the patient's LV.

13. The system of claim 12, wherein at least two of the three or more electrodes, implanted at or near the location of the patient's LV, are part of a same transvenous left ventricular lead.

14. The system of claim 12, wherein at least two of the three or more electrodes, implanted at or near the location of the patient's LV, are part of a same coronary sinus interpericardial left ventricular lead.

15. The system of claim 12, wherein at least one of the three or more electrodes, implanted at or near the location of the patient's LV, is part of a different lead than another one of the electrodes.

16. The system of claim 12, wherein the minimum acceptable potential gradient at the location of the patient's LV, where it is predicted that a potential gradient response to RV stimulation pulses will be lowest, is a potential gradient value in the range of approximately 4 Volts/cm to approximately 6 Volts/cm.

17. The system of claim 12, wherein the one or more processors
extrapolates, based on the computed potential gradients, a best fit line representative of the potential gradient at the location of the patient's LV as a function of RV stimulation energy levels, where the best fit line extends to at least the minimum acceptable potential gradient; and
estimates, based on the extrapolated best fit line, the RV stimulation energy level that is needed to achieve the minimum acceptable potential gradient at the location within the patient's LV where it is predicted that a potential gradient response to RV stimulation pulses will be lowest.

18. The system of claim 12, wherein the delivered stimulation pulses are biphasic pulses.

19. The system of claim 12, wherein at least three of the different energy levels used are greater than 10 millijoules, but not greater than 2 Joules.

20. The system of claim 10, wherein the energy level of one or more of the of the plurality of stimulation pulses delivered to the patient's RV is/are between 1 and 2 Joules.

21. A method for estimating a patient's ventricular defibrillation threshold (VDFT), comprising:
(a) delivering a plurality of stimulation pulses to the patient's right ventricle (RV), the stimulation pulses being >10 millijoules and ≦2 Joules, with one or more of the stimulation pulses being between 1 and 2 Joules;
(b) measuring voltage potentials induced in response to the RV stimulation pulses delivered at step (a), only at a location of the patient's left ventricle (LV) where it is predicted that potential gradients induced in response to RV stimulation pulses will be lowest, using a plurality of electrodes implanted at or near the location of the patient's LV where it is predicted that potential gradients induced in response to RV stimulation pulses will be lowest;
(c) using the voltage potentials measured at step (b) to compute the potential gradients induced in response to the RV stimulation pulses delivered at step (a), wherein the computed potential gradients are for the location of the patient's LV where it is predicted that potential gradients induced in response to RV stimulation pulses will be lowest; and (d) estimating the patient's VDFT by estimating, based on the potential gradients computed at step (c), the RV stimulation energy level that would be required to achieve a minimum acceptable potential gradient at the location of the patient's LV where it is predicted that potential gradients induced in response to RV stimulation pulses will be lowest.

22. The method of claim 21, wherein each said stimulation pulse delivered at step (a) is delivered during a window defined between an R-wave and a vulnerable period that follows the R-wave.

23. The method of claim 21, wherein the location within the patient's LV, where it is predicted that potential gradients induced in response to RV stimulation pulses will be lowest, is the apex of the patient's LV.

24. The method of claim 21, wherein the location within the patient's LV, where it is predicted that potential gradients induced in response to RV stimulation pulses will be lowest, is the posterior lateral wall of the patient's LV.

25. The method of claim 21, wherein the location within the patient's LV, where it is predicted that potential gradients induced in response to RV stimulation pulses will be lowest, is the apex and/or the posterior wall of the patient's LV.

* * * * *